United States Patent
Esposito et al.

(10) Patent No.: US 11,061,262 B2
(45) Date of Patent: Jul. 13, 2021

(54) PROTECTIVE CARTRIDGE AND METHOD WITH A PROTECTIVE CARTRIDGE

(71) Applicant: Optrel Holding AG, Appenzell (CH)

(72) Inventors: Martin Esposito, Rapperswil-Jona (CH); David Bischof, Sulz (AT); Markus Michler, Feldkirch (AT)

(73) Assignee: Optrel Holding AG, Appenzell (CH)

( * ) Notice: Subject to any disclaimer, the term of this patent is extended or adjusted under 35 U.S.C. 154(b) by 246 days.

(21) Appl. No.: 16/225,497

(22) Filed: Dec. 19, 2018

(65) Prior Publication Data

US 2019/0187501 A1 Jun. 20, 2019

(30) Foreign Application Priority Data

Dec. 20, 2017 (EP) .................................... 17209124

(51) Int. Cl.
| | |
|---|---|
| *G02F 1/133* | (2006.01) |
| *A61F 9/02* | (2006.01) |
| *G02F 1/1335* | (2006.01) |
| *A61F 9/06* | (2006.01) |

(52) U.S. Cl.
CPC .......... *G02F 1/13318* (2013.01); *A61F 9/023* (2013.01); *A61F 9/067* (2013.01); *G02F 1/133509* (2013.01); *A61F 2250/0053* (2013.01)

(58) Field of Classification Search
CPC ....... G02F 1/13318; A61F 9/023; A61F 9/067
See application file for complete search history.

(56) References Cited

U.S. PATENT DOCUMENTS

| 9,164,314 B2 | 10/2015 | Van Oosten |
| 2010/0040806 A1* | 2/2010 | Suzuki .................... C08L 39/04 |
| | | 428/1.31 |
| 2014/0168546 A1 | 6/2014 | Magnusson et al. |

FOREIGN PATENT DOCUMENTS

| WO | 2004/053586 A1 | 6/2004 |
| WO | 2015/034575 A1 | 3/2015 |
| WO | 2017/196721 A1 | 11/2017 |

OTHER PUBLICATIONS

Extended European Search Report dated Jun. 28, 2018 in corresponding European Patent Application No. 17209124.1 (and English translation).

European Office Action dated Apr. 3, 2020 in corresponding European Patent Application No. 17209124.1 (and English translation).

* cited by examiner

*Primary Examiner* — Lucy P Chien

(74) *Attorney, Agent, or Firm* — Posz Law Group, PLC

(57) ABSTRACT

A protective cartridge for a glare protection apparatus, includes an optical glare protection filter which, in particular, has at least one liquid crystal cell, including at least an open-loop and/or closed-loop control unit, which is configured to control and/or regulate a permeability of the optical glare protection filter, at least between at least one bright level and at least one dark level, depending on a captured work state, on an electronic signal of an external signal source and/or on light irradiation. The permeability of the optical glare protection filter at at least one bright level corresponds to a protection level of less than 2.5, preferably of at most 2.4, advantageously of at most 2.25, particularly advantageously of at most 2 and preferably of at most 1.7.

Figure 1:
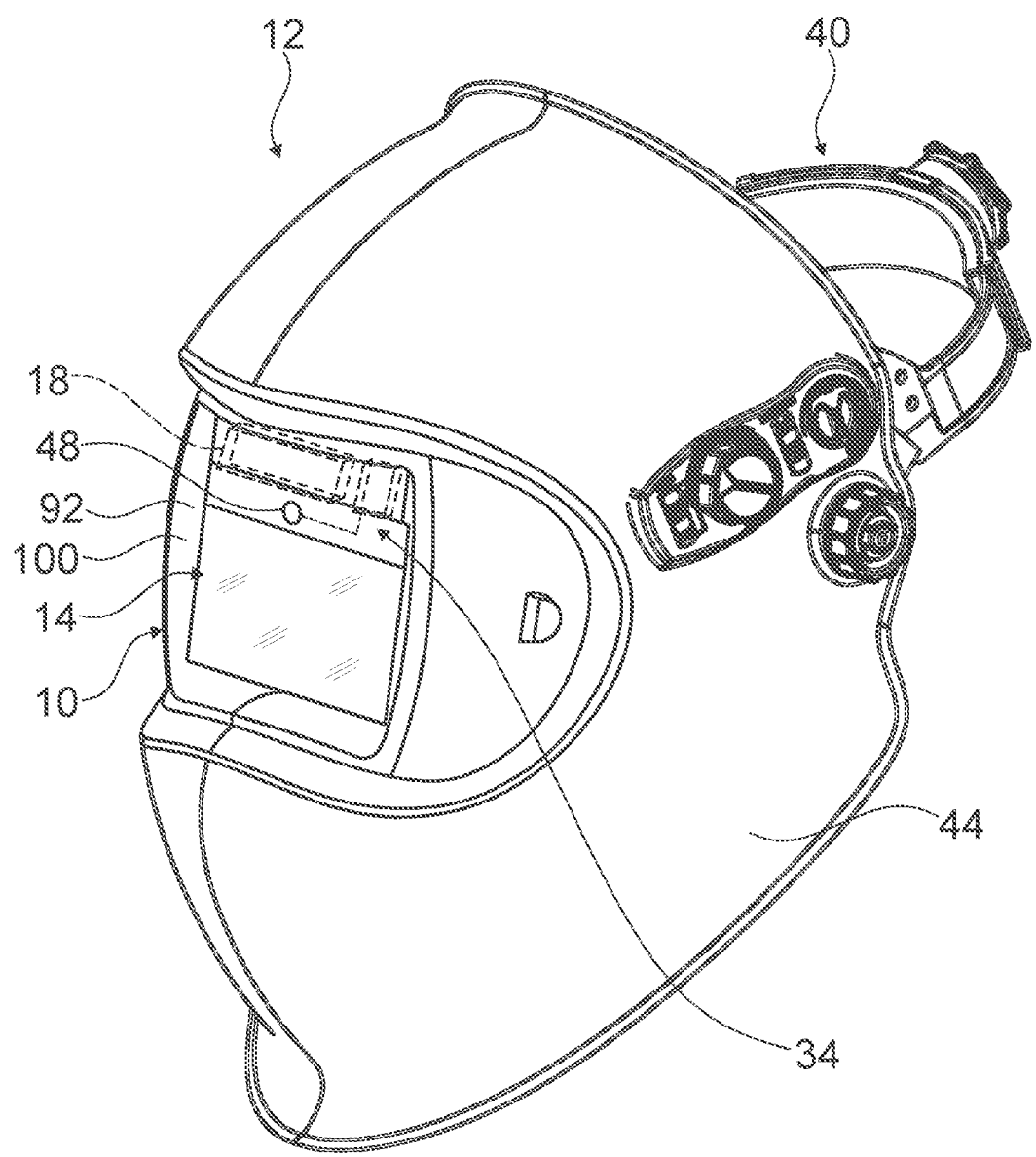

12 Claims, 4 Drawing Sheets

PROTECTIVE CARTRIDGE AND METHOD WITH A PROTECTIVE CARTRIDGE

CROSS REFERENCE TO RELATED APPLICATION

This application is based on and incorporates herein by reference European Patent Application No. 17209124.1 filed on Dec. 20, 2017.

PRIOR ART

The invention relates to a protective cartridge for a glare protection apparatus.

A protective cartridge for a glare protection apparatus, comprising an optical glare protection filter and comprising an open-loop and/or closed-loop control unit, which is configured to control and/or regulate a permeability of the optical glare protection filter, at least between at least one bright level and at least one dark level, depending on a captured work state, on an electronic signal of an external signal source and/or on light irradiation, has already been proposed. Corresponding optical glare protection filters have a low transmittance at the bright level, requiring a user of the glare protection apparatus to remove the glare protection apparatus from their field of view for reliable orientation in space and/or for a precise workpiece control of a workpiece processed by the user, possibly leading to restricted work safety and/or a restricted work speed.

The object of the invention consists, in particular, of providing a generic apparatus with improved properties in respect of a transmittance.

Advantages of the Invention

The invention proceeds from a protective cartridge for a glare protection apparatus, comprising an optical glare protection filter which, in particular, has at least one liquid crystal cell, comprising at least an open-loop and/or closed-loop control unit, which is configured to control and/or regulate a permeability of the optical glare protection filter, at least between at least one bright level and at least one dark level, depending on a captured work state, on an electronic signal of an external signal source and/or on light irradiation.

It is proposed that the permeability of the optical glare protection filter at at least one bright level corresponds to a protection level of less than 2.5, preferably of at most 2.4, advantageously of at most 2.25, particularly advantageously of at most 2, preferably of at most 1.8 and particularly preferably at least 1.7. As a result, improved properties in respect of a permeability can advantageously be achieved, in particular at at least one bright level of the optical glare protection filter. Moreover, a high level of flexibility can advantageously be achieved, in particular by virtue of being able to cover a large range of protection levels. Moreover, high user comfort can advantageously be achieved, in particular by virtue of a user being able to be provided at the bright level with a view through the optical glare protection filter that suffices for orientation in space. Advantageously, safety can be increased, in particular by virtue of being able to avoid a need for a temporary removal of the optical glare protection filter from a field of view of a user for orientation purposes and/or by virtue of being able to facilitate a risk-free orientation in space with the optical glare protection filter in the field-of-view of the user. Moreover, work can advantageously be made easier for a user, for example when using the optical glare protection filter for welding work, in particular by virtue of a result of a work step, in particular a light-emitting work step, being able to be controlled directly following the light emission, in particular without removing the optical glare protection filter from the field of view of the user. As a result, a high work speed can advantageously be achieved. In particular, the glare protection apparatus with the protective cartridge meets the requirements of the ISO 16321-1 and ISO 16321-2 standards.

Preferably, the protective cartridge is embodied as a glare protective cartridge, in particular as a welding helmet protective cartridge which, in particular, is arranged in a wearable glare protection apparatus, in particular a glare protection apparatus that can at least be placed onto the head of a user. In particular, the protective cartridge, in the worn state, is arranged in a field of view of a user and/or arranged with a secured position in relation to the eyes of the user. In particular, the protective cartridge is arranged relative to the glare protection apparatus in such a way that light emitted outside of the glare protection apparatus, and in particular emitted within a field of view of the user, can only reach the eyes of the user having been filtered by the optical glare protection filter, in particular apart from minimal stray light that is scattered from outside of the field of view. In this context, a "protective cartridge" should be understood to mean in particular a module, preferably a coherent module, of the glare protection apparatus. Preferably, particularly at least in part, the protective cartridge has a common housing, at least an essential part of the components of the protective cartridge being arranged in and/or on said housing. Preferably, this should be understood to mean a dedicated module, in particular, which is preferably functional on its own. However, in principle, it would also be conceivable for the protective cartridge to be integrated into a further unit of the glare protection apparatus, such as a shield unit and/or a welding helmet, for example. The phrase "integrated into a further unit of the glare protection apparatus" should be understood, in particular, to mean that the protective cartridge has an at least partly integral embodiment with the further unit of the glare protection apparatus and/or it is connected, at least substantially in a non-detachable manner, in particular in a manner that is not non-destructively detachable, with the further unit of the glare protection apparatus, particularly at least one housing part of the shield unit and/or of the welding helmet and/or of at least one frame part of the shield unit and/or the welding helmet and/or it forms a fixed constituent part of the glare protection apparatus. In particular, "integral" should be understood to mean cohesively connected, for example by a welding process and/or adhesive bonding process, etc., and particularly advantageously be understood to mean formed on, like in the case of the production from one cast and/or in the case of the production in a single or multicomponent injection molding method. Here, "at least substantially non-detachable manner" should be understood to mean, in particular, a connection between at least two elements that are only separable from one another if use is made of separating tools such as, e.g., a saw, in particular a mechanical saw, etc., and/or chemical separation means, such as, e.g., solvents, etc.

Further, in this context, a "glare protection apparatus" should be understood to mean, in particular, an apparatus configured to protect a user from too high brightness and/or sparks. Preferably, this should be understood to mean, in particular, an apparatus which serves to protect eyes and/or a facial region of a user during a welding, cutting, brazing and/or grinding process. Preferably, this should be understood to mean, in particular, an apparatus which, in particular, serves to protect the eyes of a user, at least during a welding process. Various configurations of a protection apparatus that appear expedient to a person skilled in the art are conceivable, such as a welding helmet, welding screen, welding mask, welding goggles and/or welding shield for example. An "optical glare protection filter" should be understood to mean, in particular, an optical filter for a glare protection apparatus which, in particular, at least comprises a protective glass and/or a plastic protective glass. In particular, the optical glare protection filter is at least configured to absorb and/or reflect at least some of a light striking the optical glare protection filter. In particular, an absorption, in particular an absorption strength, and/or reflection, in particular a reflection strength, of the optical glare protection filter is wavelength-dependent. By way of example, it is conceivable that one part of the electromagnetic spectrum, for example UV light, is absorbed and/or reflected more strongly than a further part of the electromagnetic spectrum, for example visible light. Preferably, the optical glare protection filter absorbs and/or reflects virtually all UV light, while visible light, in particular, is only absorbed and/or reflected in part by the optical glare protection filter, said part being less than 70%, in particular, preferably 60%. Preferably, an absorption, in particular an absorption strength, and/or reflection, in particular a reflection strength, of the optical glare protection filter is regulable. Preferably, the optical glare protection filter should be understood to mean, in particular, an optical filter configured with an adjustable light transmittance. Preferably, this should be understood to mean, in particular, an optical welding protection filter with automatic darkening.

Particularly preferably, the glare protection filter has at least one liquid crystal plane that is switchable in transmission, in particular at least one liquid crystal cell, preferably at least two liquid crystal cells. Various configurations of the optical glare protection filter that appear expedient to a person skilled in the art are conceivable; however, in particular, this should be understood to mean an ADF, also referred to as "automatic darkening filter" or "automatic welder protection filter". Moreover, in this context, an "open-loop and/or closed-loop control unit" should be understood to mean, in particular, a unit with at least one control electronics unit. In particular, "control electronics" should be understood to mean a unit with at least one electronic circuit which preferably consists of voltage and comparison control components. In principle, the control electronics may, however, also have a more complex design, in particular by using an application-specific integrated circuit (ASIC) and/or a microcontroller component. In particular, a "work state" should be understood to mean an operational state of at least part of a work appliance and/or tool. Preferably, the work state is embodied as an operational state of a welding, brazing and/or flame-cutting appliance such as, for example, a power supply, a fuel supply and/or an activation of the welding, brazing and/or flame-cutting appliance. It is conceivable for the glare protection apparatus to have at least one information interface for receiving at least one information item about at least one work state and/or to have at least one sensor for detecting at least one work state. In particular, the protective cartridge has at least one light sensor, in particular a light-intensity sensor which, in particular, is configured to transmit measurement data to the open-loop and/or closed-loop control unit for processing purposes. Alternatively, it is conceivable for the protective cartridge to receive at least data, for example electronic control and/or regulation signals, at least of an external light sensor, for example a light sensor of the glare protection apparatus, and/or a further external signal source and to process at least said data by means of the open-loop and/or closed-loop control unit for the purposes of controlling and/or regulating the permeability of the optical glare protection filter. In particular, a "bright level" should be understood to mean a light permeability level of the optical glare protection filter with maximum light transmission through the optical glare protection filter. Preferably, all liquid crystal cells of the optical glare protection filter are switched to maximum light permeability at the bright level. In particular, a "dark level" should be understood to mean a light permeability level of the optical glare protection filter with a reduced light transmission through the optical glare protection filter, in particular in comparison with the bright level. Preferably, at least one liquid crystal cell of the optical glare protection filter is switched in a state that reduces and/or influences a light permeability at the dark level. Preferably, the dark level, in particular the reduction of the light transmission at the dark level, is regulable in steps and/or, preferably, in continuous fashion. In particular, the dark level, in particular the reduction at the light transmission, is adjustable by the user. Preferably, the dark level, in particular the reduction in the light transmission, is automatically regulable by means of the open-loop and/or closed-loop control unit, in particular depending on a measured and/or received light intensity and/or a certain work state.

Further, various liquid crystal cells appearing expedient to a person skilled in the art are conceivable, such as, in particular, TN liquid crystal cell using twisted nematic technology. In particular, the TN liquid crystal cell can be embodied as a "normally black" TN liquid crystal cell, preferably as a "normally white" TN liquid crystal cell. However, in principle, other embodiments of the liquid crystal cells appearing expedient to a person skilled in the art would also be conceivable, such as, for example, STN liquid crystal cells using super twisted nematic technology, DSTN liquid crystal cells using double super twisted nematic technology, TSTN liquid crystal cells using triple super twisted nematic technology, VA liquid crystal cells using vertical alignment technology, in particular PVA/MVA liquid crystal cells using patterned vertical alignment and/or multi-domain vertical alignment technology, IPS liquid crystal cells using in-plane switching technology, FLCD liquid crystal cells, i.e. ferroelectric liquid crystal cells and/or TN liquid crystal cells using guest host technology. In particular, "configured" should be understood to mean specifically programmed, designed and/or equipped. An object being configured for a certain function should be understood to mean, in particular, that the object satisfies and/or carries out this specific function in at least one application and/or operational state.

In particular, a "protection level" should be understood to mean an eye protection level pursuant to the DIN EN 166:2002-04 and/or DIN EN 169:2003-02 standards. In particular, a transmission through the optical glare protection filter depends on the protection level of the optical glare protection filter. In particular, a transmission through the optical glare protection filter increases with decreasing protection level.

Furthermore, it is proposed that the permeability of the optical glare protection filter at at least one dark level corresponds to a protection level of at least 3, preferably at least 5, advantageously at least 10, particularly advantageously at least 12, preferably at least 15 and particularly preferably at most 16. Advantageously, this can achieve a high level of safety, in particular by virtue of light that poses a risk to the eyes being able to be effectively kept away from the eyes of the user. Moreover, a high level of flexibility can advantageously be achieved, in particular by virtue of being able to cover a large bandwidth of protection levels.

Moreover, it is proposed that the optical glare protection filter, at at least one bright level, has in at least one spectral range a transmittance of at least 29%, preferably of at least 33%, preferably of at least 40% and particularly preferably of at most 80%. As a result, it is advantageously possible to obtain improved properties in respect of a permeability of light, in particular at at least one bright level of the optical glare protection filter. Moreover, a high level of user comfort can advantageously be achieved, in particular by virtue of it being possible to provide a user with sufficient sight through the optical glare protection filter for an orientation in space at the bright level, as result of which, advantageously, a high level of safety can be achieved. In particular, a "spectral range" should be understood to mean at least one portion of the electromagnetic spectrum, for example an infrared region, a region of visible light, a UV region and/or an at least partial combination of the infrared region, the region of visible light and/or the UV region. Preferably, the spectral range that, in particular, has the greatest transmittance through the optical glare protection filter is embodied as at least one region of the visible light which, in particular, is delimited in the direction of the infrared region and/or the UV region. Preferably, the spectral range includes at least light in a wavelength range lying above 380 nm, preferably above 420 nm and preferably above 470 nm, and below 550 nm, preferably below 590 nm and particularly preferably below 780 nm. In particular, the value of the transmittance is embodied as a mean transmission value through the optical glare protection filter of light of the spectral range when averaging over all wavelengths of the spectral range and/or as a minimum transmission value of light with a wavelength lying within the spectral range. Additionally, a weighting factor, in particular a wavelength-dependent weighting factor, can be used, particularly when calculating the average transmission value, for example as described in the ISO 16321-1 and/or ISO 16321-2 standards.

If the optical glare protection filter has at least one further liquid crystal cell which is arranged behind and/or in front of a liquid crystal cell, in particular in a viewing direction through the optical glare protection filter, then a high level of flexibility can advantageously be achieved, in particular by virtue of being able to cover a large bandwidth of protection levels. Moreover, safety can advantageously be increased, for example by cushioning a malfunction of one liquid crystal cell by way of appropriate control and/or regulation of the other liquid crystal cell. In particular, the further liquid crystal cell has an identical embodiment to the liquid crystal cell. Alternatively, the further liquid crystal cell can embody a liquid crystal cell type that differs from the liquid crystal cell. Preferably, the control and/or regulation of the liquid crystal cell and the further liquid crystal cell is directly and/or indirectly coupled. In particular, the liquid crystal cell and/or the further liquid crystal cell is configured to at least partly filter, in particular absorb, at least UV light, at least visible light and/or at least infrared light. It is conceivable for the liquid crystal cell and the further liquid crystal cell to have at least substantially identical filter curves. Alternatively, the liquid crystal cell and the further liquid crystal cell could have at least substantially different filter curves. In particular, a "filter curve" should be understood to mean a wavelength dependence of the transmission through the liquid crystal cell.

Moreover, it is proposed that the optical glare protection filter has at least one passive filter unit. Advantageously, this allows a high level of safety to be achieved, in particular by virtue of the passive filter unit effectively absorbing and/or reflecting at least one part of the light spectrum, in particular an invisible and/or eye-damaging part of the light spectrum, such as UV radiation, for example, in a manner independent of an actuation by the open-loop and/or closed-loop control unit. As a result, a good "fail-safe" behavior of the optical glare protection filter can advantageously be achieved. In particular, the passive filter unit meets the requirements of the ISO 16321-1 and ISO 16321-2 standards. In particular, a "passive filter unit" should be understood to mean a filter unit which filters, absorbs and/or reflects electromagnetic radiation, in particular in passive fashion, with filter properties, absorption properties and/or reflection properties being uninfluenceable, uncontrollable and/or unregulable from the outside after the passive filter unit has been assembled in the protective cartridge. In particular, the passive filter unit absorbs and/or reflects, at least in part, light of at least one part of an infrared spectral range, one part of a visible spectral range and/or one part of an ultraviolet spectral range of electromagnetic radiation, at at least 5% thereof, preferably at least 10% thereof, preferably at least 15% thereof, advantageously at least 20% thereof, preferably at least 25% thereof and particularly preferably at most 90% thereof. Preferably, the filter properties, absorption properties and/or reflection properties of the components of the passive filter unit are constant and/or unchangeable over time, in particular except for material corrosion. In particular, the filter properties, absorption properties and/or reflection properties are predominantly dependent on material properties, in particular constant material properties, of the respective components and/or on an angle of incidence of striking rays. As an alternative or in addition thereto, it is conceivable for the correspondingly low protection level at the bright level to be obtained by means of an active filter unit, in particular an active filter unit that differs from the liquid crystal cells and/or that is present in addition to the liquid crystal cells, in particular while observing eye protection regulations, as demanded in at least one of the ISO 16321-1, ISO 16321-2, DIN EN 166:2002-04 and/or DIN EN 169:2003-02 standards. In particular, the active filter unit can be embodied as a transparency element, in particular a pane and/or an electrochromic device (ECD), which comprises at least one electrochromic material, for example embodied as intelligent glass which reacts to voltages and/or electromagnetic fields, in particular varies its transparency. In particular, an electrochromic material could comprise at least one electrochromic, electroactive and/or electrochemical polymer, such as an electroactive polyamide and/or heptyl viologen for example. As an alternative or in addition thereto, the passive filter unit could comprise at least one absorption film, a metal coating and/or a metalorganic coating for influencing the absorption properties and/or reflection properties of the passive filter unit.

Moreover, it is proposed that the passive filter unit comprises at least one dichroic filter element. As a result, it is advantageously possible to obtain improved properties in respect of a permeability, in particular of selected wavelength regions of electromagnetic radiation. In particular, it is advantageously possible to facilitate bright levels of the optical glare protection filter with low protection levels. Advantageously, a permeability of the passive filter unit can be restricted to a certain part of the spectrum, as a result of which a high level of safety and/or a good "fail-safe" behavior can advantageously be achieved. In particular, the dichroic filter element is embodied as at least one dichroic mirror and/or an interference filter. Preferably, the dichroic filter element is embodied as at least one coating of a substrate, in particular an at least partly transparent substrate. In particular, the coating comprises at least a plurality of partial layers lying over one another perpendicular to the substrate. In particular, the coating, preferably at least one partial layer of the coating, preferably at least two partial layers of the coating, could be formed, at least in part, from a metal, for example silver and/or aluminum. In particular, the coating is embodied as at least one layer stack made of two thin metal layers with an interposed dielectric, transparent layer. Preferably, the coating is embodied, at least in part, as at least one layer stack made of at least two dielectric, nonmetallic layers, preferably a plurality of dielectric, nonmetallic layers, lying one above other, in particular in alternating fashion, perpendicular to a surface of the substrate, said layers having different thicknesses and different refractive indices, embodying at least one Bragg mirror, in particular. In particular, the dichroic filter element is configured to reflect at least one part of the incident electromagnetic radiation, in particular the UV component and/or the IR component of the electromagnetic radiation, in particular to a level of at least 95%, and/or to transmit at least one part, in particular a further part, of the incident electromagnetic radiation, in particular the visible part of the electromagnetic radiation, in particular to a level of at least 80%. Moreover, it is conceivable for the passive filter unit to comprise at least one further dichroic filter element. As a result, a wavelength-dependent transmission through the optical glare protection filter can advantageously be set even more accurately.

Furthermore, it is proposed that the dichroic filter element implements a longpass filter or a bandpass filter. Alternatively, it is conceivable for the dichroic filter element to form a shortpass filter. As a result, it is advantageously possible to achieve improved properties in view of a permeability, in particular of selected wavelength ranges of electromagnetic radiation. Advantageously, a permeability of the passive filter unit can be restricted to certain part of the spectrum, as a result of which, advantageously, a high level of safety and/or a good "fail-safe" behavior can be obtained. In particular, a "longpass filter" should be understood to mean a filter for electromagnetic radiation which largely reflects electromagnetic radiation with a wavelength shorter than a cutoff wavelength and which largely transmits electromagnetic radiation with a wavelength greater than the cutoff wavelength. In particular, the cutoff wavelength can be selected as desired. Preferably, the cutoff wavelength lies at the edge of the visible electromagnetic spectrum, for example at 380 nm. In particular, largely should be understood to mean at least 80%, preferably at least 85%, advantageously at least 90%, preferably at least 95% and particularly preferably at least 98%. In particular, a "bandpass filter" should be understood to mean a filter for electromagnetic radiation which largely reflects electromagnetic radiation with a wavelength shorter than a first cutoff wavelength and electromagnetic radiation with a wavelength longer than a second cutoff wavelength, which differs from the cutoff wavelength, and which largely transmits electromagnetic radiation with a wavelength between the first cutoff wavelength and the second cutoff wavelength. In particular, the first cutoff wavelength and second cutoff wavelength can be selected as desired. Preferably, the first cutoff wavelength and the second cutoff wavelength each lie at the edges of the visible electromagnetic spectrum, for example at 380 nm and at 780 nm.

Moreover, it is proposed that the passive filter unit comprises at least one absorbing and/or reflecting infrared filter element, in particular at least one absorptive glass. As a result, it is advantageously possible to achieve improved properties in view of a permeability, in particular of selected wavelength ranges of electromagnetic radiation. In particular, bright levels of the optical glare protection filter with low protection levels can advantageously be facilitated. Advantageously, a permeability of the passive filter unit can be restricted to certain part of the spectrum, as a result of which, advantageously, a high level of safety and/or a good "fail-safe" behavior can be obtained. Moreover, this can advantageously keep invisible and/or eye-damaging infrared light away from the user's eye in a large part. In particular, the infrared filter element is configured to largely absorb and/or reflect electromagnetic radiation in a wavelength range above and including 780 nm. An absorptive glass comprises, in particular, glass, in particular colored glass, a dye, in particular, having been added thereto, said dye being configured, in particular, for absorbing infrared radiation. By way of example, the dye comprises iron (II) oxide, iron (III) oxide and/or copper (II) oxide. In particular, the infrared filter element can form a shortpass filter. In particular, the infrared filter element, in particular the absorptive glass, can be formed only partly from colored glass. By way of example, the infrared element, in particular the absorptive glass, could comprise a layer structure, with one layer, in particular, causing a high absorption of infrared radiation. Individual layers of the layer structure can be cohesively connected, in particular. In particular, "cohesively connected" should be understood to mean that the mass parts are held together by atomic or molecular forces, like in the case of adhesive bonding, laminating and/or vulcanizing, for example. As an alternative or in addition thereto, the infrared filter element, in particular the absorptive glass, may have a vapored coating, in particular a coating applied by sputtering, and/or a coating applied by a further coating method, said coating being configured to absorb infrared radiation. Moreover, it is conceivable for individual layers of the layer structure of the infrared filter element, in particular of the absorptive glass, and/or a connecting layer of the infrared filter element, in particular the absorptive glass, to be connected to at least one element adjoining the infrared filter element, in particular the absorptive glass, for example the dichroic filter element, for a connection of the infrared filter element, in particular the absorptive glass, by means of an adhesive, which, in particular, forms a layer that efficiently absorbs infrared radiation and consequently preferably at least partly forms the infrared filter element, in particular the absorptive glass. In particular, the infrared filter element can form a bandpass filter in combination with a dichroic mirror that forms a longpass filter.

Further, it is proposed that the passive filter unit has, in at least one spectral range, in particular in a visible spectral range, preferably in a spectral range that forms a restricted bandwidth, a transmittance of at least 80%, preferably at least 85%, preferably at least 90% and particularly preferably at most 95%. As a result, improved properties can advantageously be obtained in view of a permeability, in particular of selected wavelength ranges of electromagnetic radiation. Moreover, a high level of user comfort can advantageously be achieved, in particular by virtue of it being possible to provide a user with sufficient sight through the optical glare protection filter for an orientation in space at the bright level. Moreover, a level of safety for the user can advantageously be increased thereby. In particular, the "restricted bandwidth" comprises a wavelength range lying above 380 nm, preferably above 420 nm and preferably above 470 nm, and below 550 nm, preferably below 590 nm and particularly preferably below 780 nm.

Furthermore, it is proposed that the passive filter unit has a transmittance of at most 5%, preferably at most 2%, preferably at most 1% and particularly preferably 0% in at least one further spectral range, in particular a restricted spectral range, preferably an ultraviolet spectral range. As a result, a high level of safety can advantageously be achieved, in particular by virtue of being able to keep eye-damaging and/or invisible UV radiation away from the user's eye. In particular, the further spectral range comprises light with wavelengths of at least less than 470 nm, preferably at least less than 420 nm, preferably at least less than 380 nm and particular preferably at least less than 350 nm.

Moreover, it is proposed that the optical glare protection filter comprises at least one antireflection unit. As a result, improved properties in respect of a permeability can advantageously be obtained. In particular, the antireflection unit is arranged on a side of the optical glare protection filter facing the user's eye in the worn state. As an alternative or in addition thereto, the antireflection unit can be arranged on a side of the optical glare protection filter facing away from the user's eye in the worn state. The antireflection unit is configured to bring about a reduction in a reflection in at least one spectral range, preferably in a spectral range including visible light which is delimited, in particular, by wavelengths above 380 nm, preferably above 420 nm and preferably above 470 nm, and/or below 550 nm, preferably below 590 nm and particularly preferably below 780 nm, said reduction in reflection bringing about an increase in a transmittance of the optical glare protection filter by at least 2%, preferably by at least 3% and preferably by at least 4%, particularly in the spectral range. In particular, the antireflection unit comprises at least one interference filter, in particular with at least one antireflection coating and/or with at least a plurality of antireflection coatings. As an alternative or in addition thereto, the antireflection unit may comprise at least one nanostructured surface that exploits the "moth's eye effect", at least one refractive-index-reducing surface structure and/or at least one circular polarizer.

Further, a glare protection apparatus comprising a protective cartridge is proposed. As a result, a high level of user comfort can advantageously be achieved, in particular by virtue of a user being able to be provided at the bright level with a view through the optical glare protection filter that suffices for orientation in space. Advantageously, safety can be increased, in particular by virtue of being able to avoid a need for a temporary removal of the optical glare protection filter from a field of view of a user for orientation purposes and/or by virtue of being able to facilitate a risk-free orientation in space with the optical glare protection filter in the field-of-view of the user. Moreover, work can advantageously be made easier for a user, for example when using the optical glare protection filter for welding work, in particular by virtue of a result of a work step, in particular a light-emitting work step, being able to be controlled directly following the light emission, in particular without removing the optical glare protection filter from the field of view of the user. As a result, a high work speed can advantageously be achieved.

Moreover, a method with a protective cartridge is proposed. As a result, improved properties in respect of a permeability of light can advantageously be achieved.

Moreover, a method for producing a protective cartridge is proposed, wherein, in at least one method step, a dichroic filter element is vapor-coated onto a substrate, in particular a substrate that is at least partly embodied as an absorptive glass, in particular by means of chemical gas phase deposition. As a result, improved properties in respect of a permeability can advantageously be achieved. As an alternative or in addition thereto, the dichroic filter element can be applied to the substrate, in particular the absorptive glass, by means of physical gas phase deposition and/or sputtering.

Here, the protective cartridge according to the invention and/or the method according to the invention should not be restricted to the above-described application and embodiment. In particular, the protective cartridge according to the invention and/or the method according to the invention can have a number deviating from a number of individual elements, components and units mentioned herein for the purposes of satisfying a functionality described herein.

DRAWINGS

Further advantages emerge from the following description of the drawings. An exemplary embodiment of the invention is illustrated in the drawings. The drawings, the description and the claims contain several features in combination. Expediently, a person skilled in the art will also consider the features individually and combine these to form expedient further combinations.

Figure 2:
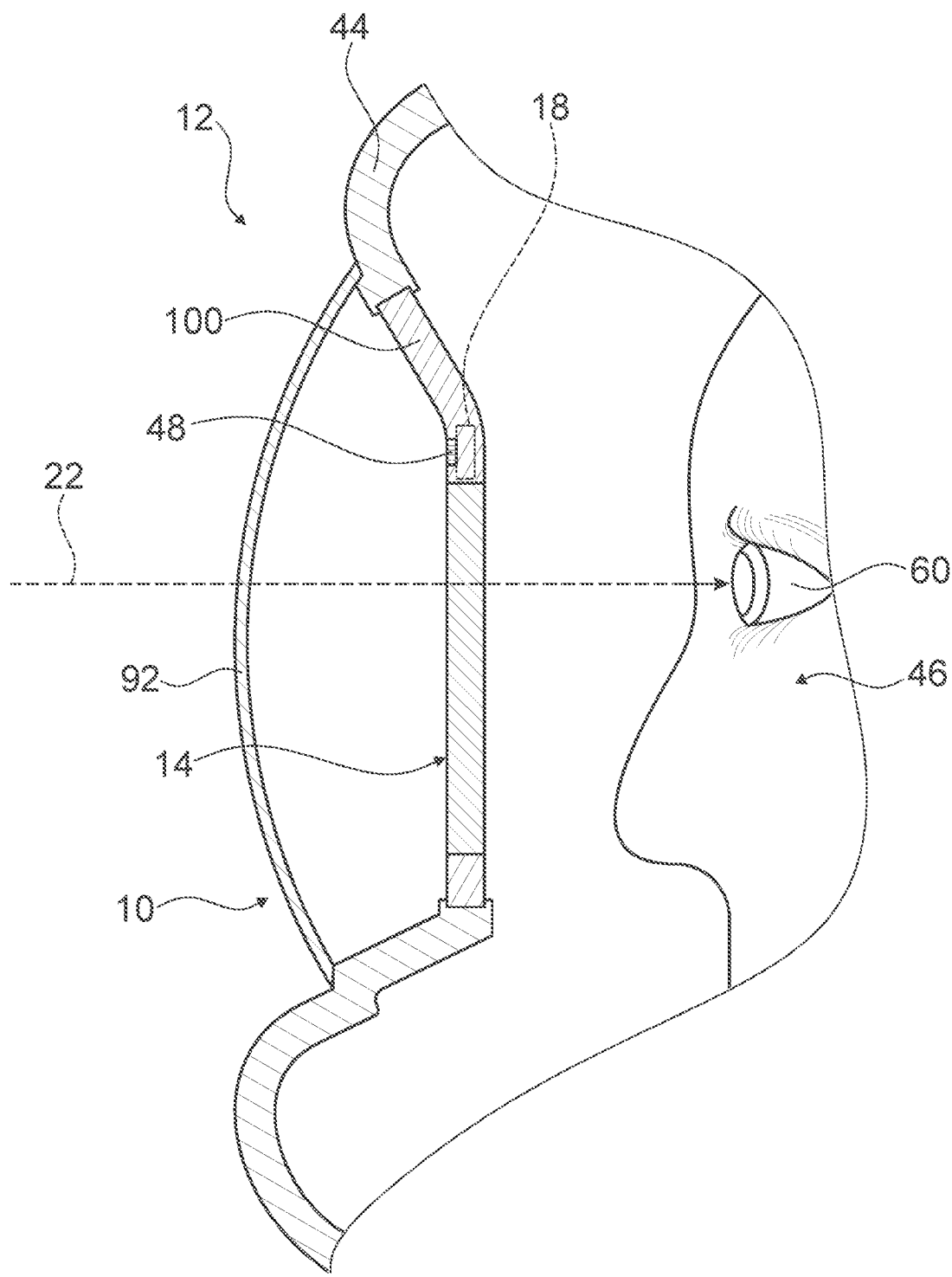
Figure 3:
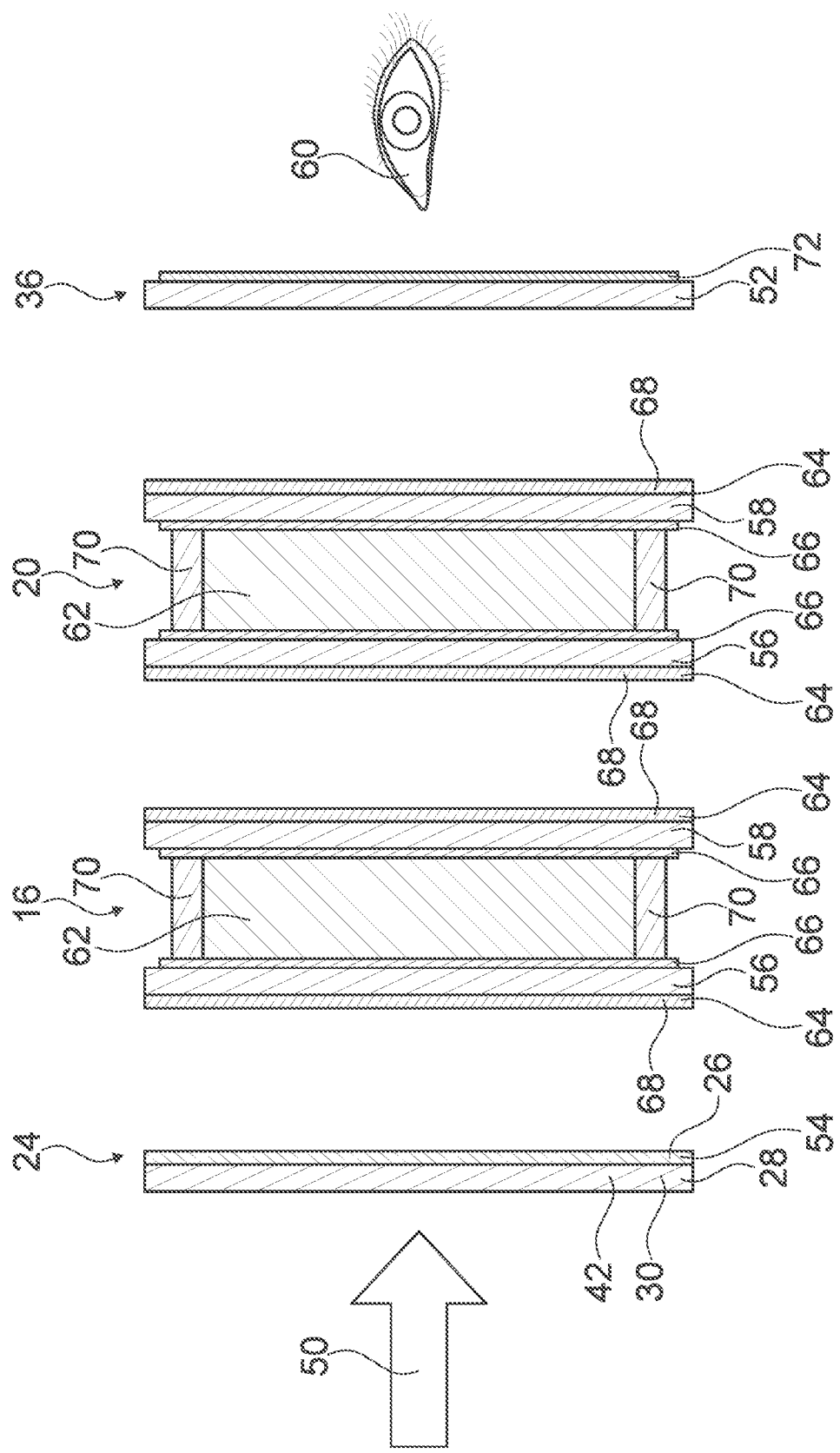
Figure 4:
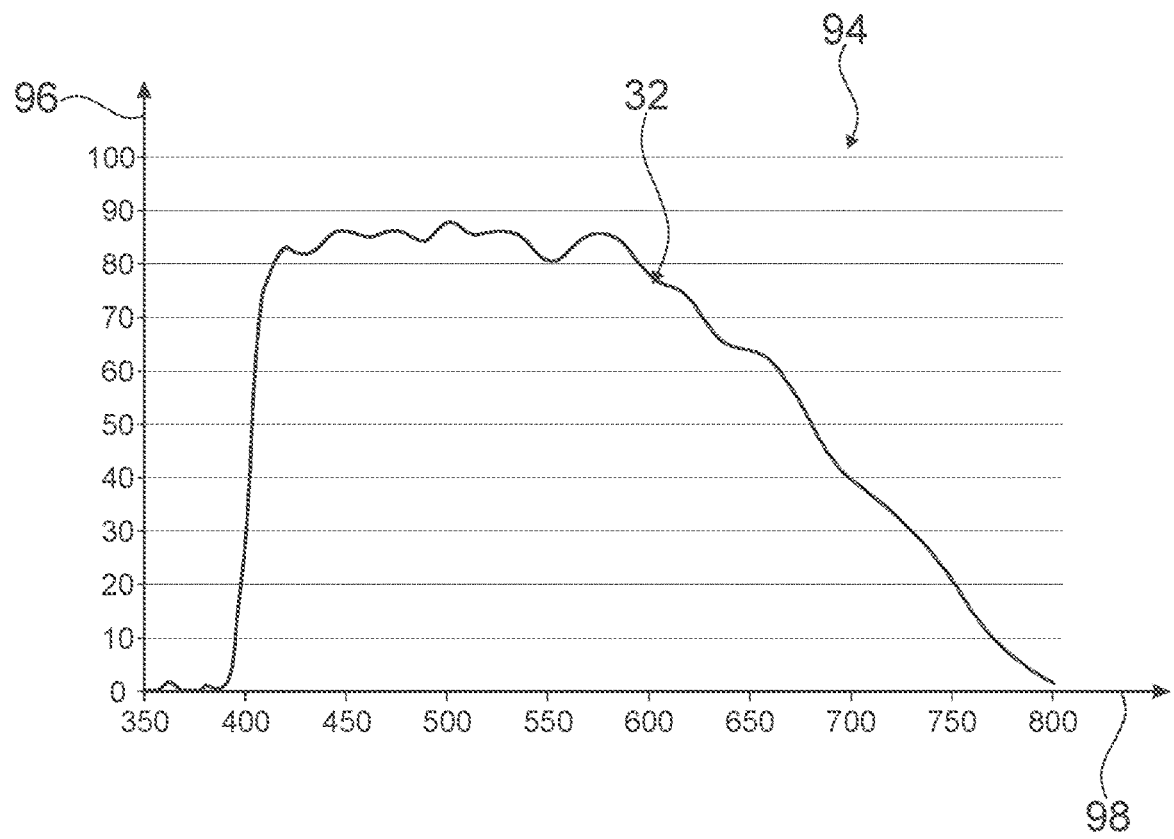
Figure 5:
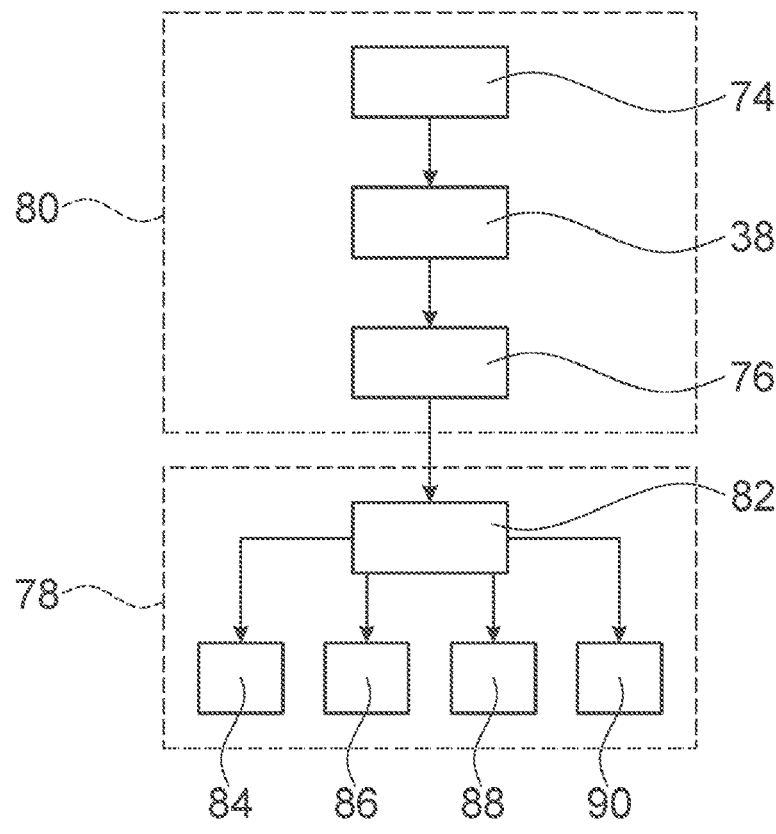

In the figures:

FIG. 1 shows a perspective schematic view of a glare protection apparatus with a protective cartridge, FIG. 2 shows a schematic sectional view of the glare protection apparatus with the protective cartridge in the worn state, FIG. 3 shows a schematic side view of an optical glare protection filter of the protective cartridge in an exploded view, FIG. 4 shows a transmittance-wavelength diagram of part of the optical glare protection filter, and FIG. 5 shows a flowchart of a method with the protective cartridge and a method for producing the protective cartridge.

DESCRIPTION OF THE EXEMPLARY EMBODIMENT

FIG. 1 shows a glare protection apparatus 12. The glare protection apparatus 12 is embodied as a welding helmet. However, in principle, any other embodiment of the glare protection apparatus 12 appearing expedient to a person skilled in the art would be conceivable. The glare protection apparatus 12 is configured to be worn on the head by an operator during operation (see also FIG. 2). Here, the operator is formed by a wearer. The glare protection apparatus 12 has a main body 44. The main body 44 surrounds a face 46 of a user. The main body 44 forms a light-opaque shield that shields the face 46 of the user. The main body 44 is formed from a heat resistant material that is hardly flammable, for example polyamide. The glare protection apparatus 12 has a head fastening unit 40. The head fastening unit 40 is configured for fastening to the head of the operator. The head fastening unit 40 is formed by a headband. The head fastening unit 40 is connected to the main body 44 in a manner that is not visible in any more detail.

The glare protection apparatus 12 comprises a protective cartridge 10. The protective cartridge 10 comprises an optical glare protection filter 14. The protective cartridge 10 comprises a covering panel 92. The covering panel 92 is configured to protect the optical glare protection filter 14. It is conceivable for the covering panel 92 to have an antireflection-coated embodiment. The optical glare protection filter 14 comprises a liquid crystal cell 16. The optical glare protection filter 14 comprises a further liquid crystal cell 20 (see FIGS. 2 and 3). The liquid crystal cell 16 and the further liquid crystal cell 20 have different external dimensions. Alternatively, the liquid crystal cell 16 and the further liquid crystal cell 20 could have at least substantially identical external dimensions. The liquid crystal cell 16 and the further liquid crystal cell 20 are arranged in succession in a viewing direction 22 through the optical glare protection filter 14. The viewing direction 22 is formed as a connecting line that connects the protective cartridge 10 and the eye 60 of the user, said connecting line being perpendicular to a surface of the protective cartridge 10. The liquid crystal cell 16 and the further liquid crystal cell 20 adjoin one another with contact. The liquid crystal cell 16 and the further liquid crystal cell 20 are adhesively bonded to one another. The liquid crystal cell 16 and the further liquid crystal cell 20 are embodied as "normally white" TN liquid crystal cells. However, in principle, another embodiment of the liquid crystal cells 16, 20 appearing expedient to a person skilled in the art would also be conceivable.

Further, the protective cartridge 10 comprises an open-loop and closed-loop control unit 18. The open-loop and closed-loop control unit 18 is configured to control a permeability of the optical glare protection filter 14 depending on a captured work state and on a light irradiation. The open-loop and closed-loop control unit 18 is configured to regulate a permeability of the optical glare protection filter 14 depending on a captured work state, on an electronic signal of an external signal source or a light irradiation. The protective cartridge 10 comprises a sensor unit 34. The open-loop and closed-loop control unit 18 is connected to the sensor unit 34. The sensor unit 34 is configured to capture a work state and/or a light irradiation. The sensor unit 34 comprises at least one sensor 48. The sensor 48 is configured to detect a welding process or the occurrence of a bright light that could damage the eyes 60 of a user or influence the latter in any other way. The sensor 48 of the sensor unit 34 is formed by a photodiode. However, in principle, any other embodiment of the sensor 48 of the sensor unit 34 appearing expedient to a person skilled in the art would also be conceivable.

The protective cartridge 10 comprises a housing 100. The optical glare protection filter 14 is partly received in the housing 100. The open-loop and closed-loop control unit 18 is received in the housing 100. The sensor unit 34 is received in the housing 100. During operation of the glare protection apparatus 12, the sensor 48 of the sensor unit 34 is partly arranged on an outer side of the protective cartridge 10 that faces away from the face 46 of the user. The housing 100 of the protective cartridge 10 is insertable into the glare protection apparatus 12 and/or removable from the glare protection apparatus 12. As a result, a simple replacement can advantageously be facilitated for repair, servicing and/or change of the protective cartridge 10.

The open-loop and closed-loop control unit 18 is configured for processing data of the sensor unit 34 and for actuating the optical glare protection filter 14 and/or the liquid crystal cell 16 and the further liquid crystal cell 20 dependent thereon. The optical glare protection filter 14 has a permeability for electromagnetic radiation. The permeability of the optical glare protection filter 14 for electromagnetic radiation is regulable and/or controllable. The open-loop and closed-loop control unit 18 is configured to control the optical glare protection filter 14 between a bright level and dark levels. The open-loop and closed-loop control unit 18 is configured to regulate the optical glare protection filter 14 between a bright level and various dark levels.

The permeability of the optical glare protection filter 14 at the bright level corresponds to a protection level of less than 2.5. The permeability of the optical glare protection filter 14 at the bright level corresponds to a protection level greater than 1.7. The permeability of the optical glare protection filter 14 at one of the dark levels corresponds to a protection level of 3. A minimum permeability of the optical glare protection filter 14 at one of the dark levels corresponds to a protection level of 16. At the bright level, the optical glare protection filter 14 has a transmittance 32 of at least 29% in a spectral range of visible light.

FIG. 3 shows a schematic side view of the optical glare protection filter 14. A typical direction of incidence 50 for electromagnetic radiation to be shielded is indicated by the direction of the arrow. A position of a user is indicated by way of an eye 60 on a side of the optical glare protection filter 14 lying opposite to the direction of incidence 50. The optical glare protection filter 14 comprises a cover panel 30. The optical glare protection filter 14 comprises a further cover panel 52. In the viewing direction 22, the liquid crystal cell 16 and the further liquid crystal cell 20 are arranged between the cover panel 30 and the further cover panel 52. The cover panel 30 is arranged on a side of the optical glare protection filter 14 facing away from the user in the worn state. The further cover panel 52 is arranged on a side of the optical glare protection filter 14 facing the user in the worn state. The cover panel 30 and the further cover panel 52 are configured for protecting the liquid crystal cell 16 and the further liquid crystal cell 20 and the constituent parts thereof.

The optical glare protection filter 14 comprises a transparency element 56. The optical glare protection filter 14 comprises a further transparency element 58. The transparency elements 56, 58 are embodied as glass panels. In the viewing direction 22, the liquid crystal cells 16, 20 are each delimited on both sides by transparency elements 56, 58. The transparency elements 56, 58 are coated. The transparency elements 56, 58 each have a coating 66 on a surface. The coating 66 of the transparency elements 56, 58 is embodied as an indium tin oxide layer (ITO). As an alternative or in addition thereto, the coating 66 can be embodied, at least in part, as an AZO coating and/or as an Si nanowire coating and/or the transparency elements 56, 58 may comprise at least one further coating made of one of the aforementioned materials. However, in principle, further embodiments and/or configurations of the coating 66 appearing expedient to a person skilled in the art are also conceivable. The coating 66 of the transparency elements 56, 58 is configured to form a transparent electrode layer. The coating 66 of the transparency elements 56, 58 is arranged on the surfaces of the transparency elements 56, 58 facing an interior of the respective liquid crystal cell 16, 20. The transparency elements 56, 58 each comprise a further coating 64 on a further surface. The coating 66 of the transparency elements 56, 58 and the further coating 64 of the transparency elements 56, 58 are arranged on opposite surfaces of the transparency elements 56, 58. The liquid crystal cells 16, 20 comprise polarization elements 68. The polarization elements 68 have an integral embodiment with the further coating 64 of the transparency elements 56, 58. The further coating 64 forms a polarization element 68. The polarization elements 68 are each arranged on the surface of the transparency elements 56, 58 facing away from the interior of the respective liquid crystal cell 16, 20. The polarization elements 68 are embodied as polarization filters. The polarization elements 68 have a preferred direction of polarization. The polarization elements 68 are configured to filter out, in particular transmit, light of a preferred direction of polarization from the incident light. The preferred directions of polarization of the polarization elements 68 of the liquid crystal cells 16, 20 are aligned in crossed fashion, in particular in perpendicular fashion, relative to one another. Alternatively, it is conceivable for at least one or more polarization elements 68 to have at least partly different preferred directions of polarization, for example preferred directions of polarization that are perpendicular to one another.

The liquid crystal cells 16, 20 each have an active layer 62. The active layer 62 is configured to manipulate a direction of polarization of incident light by means of an actuation by the open-loop and/or closed-loop control unit 18. The active layer 62 is configured to rotate the direction of polarization of light rays depending on an applied voltage. The active layer 62 is at least partly liquid. The active layer 62 is embodied as a liquid crystal layer. The active layer 62 is delimited by the coatings 66 of the transparency elements 56, 68 in the viewing direction 22. The liquid crystal cells 16, 20 each have edge seals 70. The edge seals 70 are configured to delimit the active layer 62 in directions perpendicular to the surfaces of the transparency elements 56, 58. The edge seals 70 are configured to keep the active layer 62 in the interior of the liquid crystal cells 16, 20.

The optical glare protection filter 14 comprises a passive filter unit 24. The passive filter unit 24 comprises an absorptive infrared filter element 28. The infrared filter element 28 is embodied as an absorptive glass. The infrared filter element 28 has an integral embodiment with the cover panel 30. The passive filter unit 24 comprises a dichroic filter element 26. The dichroic filter element 26 forms a longpass filter. Alternatively, the dichroic filter element 26 can form a bandpass filter. In combination, the dichroic filter element 26 and the infrared filter element 28 form a bandpass filter. The dichroic filter element 26 is embodied as a coating 54. The coating 54 is embodied as a layer stack of dielectric layers. The dichroic filter element 26 is cohesively connected, in particular adhesively bonded, to the cover panel 30. The dichroic filter element 26 is arranged on a side of the cover panel 30 facing the user in the worn state. The dichroic filter element 26 is arranged on a side of the cover panel 30 facing the liquid crystal cell 16. As an alternative or in addition thereto, the dichroic filter element 26 can also be arranged on a side of the cover panel facing away from the user in the worn state and/or on both sides of the cover panel.

In a visible spectral range, the dichroic filter element 26 has a transmittance 32 of more than 80%. In a visible spectral range, the infrared element 28 has a transmittance 32 of more than 80%. The passive filter unit 24 has a transmittance 32 of more than 80% in a visible spectral range with wavelengths between 410 nm and 590 nm (see FIG. 4). In an infrared spectral range, the infrared filter element 28 has a transmittance 32 of less than 2%. In particular, an "infrared spectral range" should be understood to mean a wavelength range of electromagnetic radiation extending between the wavelengths of 780 nm and 3000 nm. In an infrared spectral range with wavelengths above 780 nm, the passive filter unit 24 has a transmittance 32 of less than 2% (see FIG. 4). A mean value of a transmittance of the entire optical glare protection filter 14, in particular of the passive filter unit 24, is less than 1% when averaging the transmittances of all wavelengths of the infrared spectral range. In an ultraviolet spectral range, the dichroic filter element 26 has a transmittance 32 of less than 2%. In an ultraviolet spectral range of wavelengths below 390 nm, the passive filter unit 24 has a transmittance 32 of less than 2% (see FIG. 4).

The optical glare protection filter 14 comprises an antireflection unit 36. The antireflection unit 36 has an antireflection coating 72. The antireflection coating 72 is arranged on a surface of the further cover panel 52. The antireflection coating 72 is arranged on the surface of the cover panel 52 facing a user in the worn state. The antireflection coating 72 is embodied as an interference filter. However, in principle, any other embodiments of the antireflection coating 72 appearing expedient to a person skilled in the art would also be conceivable. The antireflection unit 36 is configured to increase a transmission through the optical glare protection filter 14. The antireflection unit 36 is configured to reduce a reflection on the surface of the further cover panel 52 by influencing a refractive-index-difference between air and cover panel material.

FIG. 4 shows a transmittance-wavelength diagram 94 of the cover panel 30 with the infrared filter element 28 and of the dichroic filter element 26. A wavelength of electromagnetic radiation in nanometers is plotted on the abscissa 98 of the transmittance-wavelength diagram 94. A transmittance 32 through the cover panel 30 with the infrared filter element 28 and through the dichroic filter element 26 in percent is plotted on the ordinate 96 of the transmittance-wavelength diagram 94. The transmittance 32 specifies a wavelength-dependent component of all the light incident on an outer side of the cover panel 30, which light passes through the cover panel 30 with the infrared filter element 28 and the dichroic filter 26 and which consequently, in particular, emerges again on an outer side of the dichroic filter element 26 facing away from the cover panel 30. As an alternative or in addition thereto, the transmittance 32 should be understood to mean a wavelength-dependent portion of all the light incident on the outer side of the dichroic filter element 26 facing away from the cover panel 30, which emerges on the outer side of the cover panel 30 again. In particular, the transmittance 32 or the value of the transmittance 32 has the same magnitude in both aforementioned directions. In a range of wavelengths between 410 nm and 590 nm, the transmittance 32 is greater than 80%. In a range of wavelengths between 400 nm and 680 nm, the transmittance 32 is greater than 50%. In a range of wavelengths of less than 390 nm, the transmittance 32 is less than 2%. In a range of wavelengths longer than 800 nm, the transmittance 32 is less than 2%.

FIG. 5 shows a flowchart of a method 78 with a protective cartridge 10 and of a method 80 for producing a protective cartridge 10. In principle, it is conceivable for the method 78 and/or the method 80 to include further method steps, method partial steps and/or method intermediate steps that are not shown in FIG. 5. A substrate 42 is provided in at least one method step 74. The substrate 42 is embodied as the cover panel 30. The dichroic filter element 26 is vapor deposited onto the substrate 42 in at least one further method step 38. A gas phase deposition is brought about by means of chemical gas phase deposition. However, in principle, any other coating method appearing expedient to a person skilled in the art would also be conceivable. The substrate 42 with the vapor-deposited dichroic filter element 26 is installed in a protective cartridge 10 for a glare protection apparatus 12 in at least one further method step 76. The glare protection apparatus 12 with the protective cartridge 10 is put into operation in at least one further method step 82. The glare protection apparatus 12 is operated at a bright level in which the permeability of the optical glare protection filter 14 corresponds to a protection level of less than 2.5 in at least one further method step 84. The glare protection apparatus 12 is operated at a bright level in which the permeability of the optical glare protection filter 14 corresponds to a protection level of less than 2.25 in at least one further method step 86. The glare protection apparatus 12 is operated at a bright level in which the permeability of the optical glare protection filter 14 corresponds to a protection level of less than 2 in at least one further method step 88. The glare protection apparatus 12 is operated at a dark level in which the permeability of the optical glare protection filter 14 corresponds to a protection level of 8 or more in at least one further method step 90.

REFERENCE SIGNS

10 Protective cartridge
12 Glare protection apparatus
14 Optical glare protection filter
16 Liquid crystal cell
18 Open-loop and/or closed-loop control unit
20 Further liquid crystal cell
22 Viewing direction
24 Passive filter unit
26 Dichroic filter element
28 Infrared filter element
30 Cover panel
32 Transmittance
34 Sensor unit
36 Antireflection unit
38 Method step
40 Head fastening unit
42 Substrate
44 Main body
46 Face
48 Sensor
50 Direction of incidence
52 Further cover panel
54 Coating
56 Transparency element
58 Further transparency element
60 Eye
62 Active layer
64 Further coating
66 Coating
68 Polarization element
70 Edge seal
72 Antireflection coating
74 Method step
76 Method step
78 Method
80 Method
82 Method step
84 Method step
86 Method step
88 Method step
90 Method step
92 Covering panel
94 Transmittance-wavelength diagram
96 Ordinate
98 Abscissa
100 Housing

The invention claimed is:

1. A protective cartridge for a glare protection apparatus, comprising an optical glare protection filter which, in particular, has at least one liquid crystal cell, comprising at least an open-loop and/or closed-loop control unit, which is configured to control and/or regulate a permeability of the optical glare protection filter, at least between at least one bright level and at least one dark level, depending on a captured work state, on an electronic signal of an external signal source and/or on light irradiation, wherein the glare protection apparatus has at least one information interface for receiving at least one information item about at least one work state and/or has at least one sensor for detecting the at least one work state, wherein the permeability of the optical glare protection filter at at least one bright level corresponds to a protection level of less than 2.5, wherein the optical glare protection filter has at least one passive filter unit, which comprises at least one dichroic filter element forming a long pass filter, and which comprises at least one absorbing and/or reflecting infrared filter element, wherein the infrared filter element has an integral embodiment with a cover panel, which is arranged on a side of the optical glare protection filter facing away from a user in a worn state, wherein the at least one dichroic filter element is configured to reflect at least one part of incident electromagnetic radiation, namely a UV component of the electromagnetic radiation, wherein the optical glare protection filter comprises an antireflection unit, which has an antireflection coating arranged on a surface of a cover panel facing the user in the worn state, further wherein the antireflection unit is arranged on a side of the optical glare protection filter facing away from an eye of the user in the worn state.

2. The protective cartridge as claimed in claim 1, wherein the permeability of the optical glare protection filter at at least one dark level corresponds to a protection level of at least 3, preferably at least 5, advantageously at least 10, particularly advantageously at least 12, preferably at least 15 and particularly preferably at most 16.

3. The protective cartridge as claimed in claim 1, wherein the optical glare protection filter, at at least one bright level, has a transmittance of at least 29%, preferably of at least 33%, preferably of at least 40% and particularly preferably of at most 80% in at least one spectral range.

4. The protective cartridge as claimed in claim 1, wherein the optical glare protection filter has at least one further liquid crystal cell which is arranged behind and/or in front of a liquid crystal cell, in particular in a viewing direction through the optical glare protection filter.

5. The protective cartridge as claimed in claim 1, wherein the passive filter unit has a transmittance of at least 80%, preferably at least 85%, preferably at least 90% and particularly preferably at most 90% in at least one spectral range.

6. The protective cartridge as claimed in claim 1, wherein the passive filter unit has a transmittance of at most 5%, preferably at most 2%, preferably at most 1% and particularly preferably 0% in at least one spectral range.

7. A glare protection apparatus comprising a protective cartridge as claimed in claim 1.

8. A method with a protective cartridge as claimed in claim 1.

9. A method for producing a protective cartridge as claimed in claim 1.

10. The method as claimed in claim 9, wherein the dichroic filter element is vapor-coated onto a substrate, in particular a substrate that is at least partly embodied as an absorptive glass, in particular by means of chemical gas phase deposition, in at least one method step.

11. The protective cartridge as claimed in claim 4, wherein the dichroic filter element is embodied as at least one coating of an at least partly transparent substrate, wherein the dichroic filter element is arranged on a side of the cover panel facing the liquid crystal cell.

12. The protective cartridge as claimed in claim 1, wherein the infrared filter element is embodied as an absorptive glass.

* * * * *